(12) United States Patent
McVey et al.

(10) Patent No.: US 8,357,331 B2
(45) Date of Patent: Jan. 22, 2013

(54) FEED BACK AND DOSE CONTROL OF DISTRIBUTED DECONTAMINATION SYSTEMS

(75) Inventors: Iain F. McVey, Lakewood, OH (US); Aaron L. Hill, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 554 days.

(21) Appl. No.: 12/570,051

(22) Filed: Sep. 30, 2009

(65) Prior Publication Data

US 2011/0076189 A1 Mar. 31, 2011

(51) Int. Cl.
- *G01D 11/26* (2006.01)
- *G01N 21/00* (2006.01)
- *G05B 19/18* (2006.01)
- *G05B 11/01* (2006.01)

(52) U.S. Cl. ............. 422/28; 422/1; 422/3; 422/62; 422/108; 422/119; 700/2; 700/8; 700/20

(58) Field of Classification Search ............ 422/1, 3, 422/28, 108, 119, 62; 700/2, 8, 20
See application file for complete search history.

(56) References Cited

U.S. PATENT DOCUMENTS

| | | | |
|---|---|---|---|
| 5,600,142 A | 2/1997 | Van Den Berg et al. | |
| 5,792,435 A | 8/1998 | Mueller et al. | |
| 5,847,392 A | 12/1998 | Van Den Berg et al. | |
| 5,847,393 A | 12/1998 | Van Den Berg et al. | |
| 5,872,359 A | 2/1999 | Stewart et al. | |
| 5,882,590 A | 3/1999 | Stewart et al. | |
| 6,077,480 A | 6/2000 | Edwards et al. | |

FOREIGN PATENT DOCUMENTS

| | | | |
|---|---|---|---|
| WO | 98/57673 | | 12/1998 |
| WO | WO 98/57673 | * | 12/1998 |
| WO | 2005/035067 | | 4/2005 |
| WO | 2006/031957 | | 3/2006 |

OTHER PUBLICATIONS

International Preliminary Report on Patentability from corresponding PCT Application No. PCT/US2010/047469 mailed Dec. 9, 2011.
International Search Report and the Written Opinion of the International Searching Authority from the corresponding International Application No. PCT/US2010/047469 mailed Nov. 12, 2010.

* cited by examiner

*Primary Examiner* — Jill Warden
*Assistant Examiner* — Monzer Chorbaji
(74) *Attorney, Agent, or Firm* — Renner, Otto, Boisselle & Sklar, LLP

(57) ABSTRACT

A sterilization system includes a plurality of vaporizers that are controlled by a network of interconnected controllers. The network includes a plurality of control units with each control unit controlling an associated vaporizer to adjust independently the rate at which the associated vaporizer injects vaporized sterilant into the different regions of an enclosure. The network also includes a master control unit configured to control each control unit over the network to coordinate the aggregate injection of sterilant vapor.

9 Claims, 4 Drawing Sheets

FEED BACK AND DOSE CONTROL OF DISTRIBUTED DECONTAMINATION SYSTEMS

TECHNICAL FIELD

This invention relates to decontamination systems and to a decontamination process.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

A decontamination system is provided that includes a plurality of decontaminant sources that are integrated into a network to permit a more effective and efficient distribution of decontaminant throughout the space being decontaminated.

According to an aspect of the disclosure, a sterilization system includes a source of a liquid sterilant; a plurality of vaporizers that independently inject vaporized sterilant into a carrier gas at differently adjustable rates, each vaporizer including a separate liquid sterilant regulator for simultaneously, variably, and independently controlling a rate of injection of sterilant into the vaporizer; at least one supply line for transporting the sterilant vapor from each vaporizer to different regions of an enclosure to be sterilized; and a network of interconnected controllers including (a) a plurality of control units, each control unit controlling an associated vaporizer to adjust independently the rate at which the associated vaporizer injects vaporized sterilant so as to provide each of the regions with a selected concentration of sterilant vapor, and (b) a master control unit configured to control each control unit over the network to coordinate the aggregate injection of sterilant vapor.

According to an embodiment of the sterilization system, the master control unit is one of the plurality of control units.

According to another embodiment of the sterilization system, the master control unit is a separate unit from the plurality of control units.

According to an embodiment of the sterilization system, the sterilization system includes a plurality of monitors for detecting conditions in each of the different regions of the enclosure, and the network of interconnected controllers controls the rate at which each vaporizer injects vaporized sterilant into the carrier gas in accordance with the detected conditions in the different regions. The detected conditions may be chosen from temperature, pressure, relative humidity, air flow velocity, sterilant concentration and combinations thereof.

According to one embodiment of the sterilization system, the sterilant comprises hydrogen peroxide.

According to another embodiment of the sterilization system, each vaporizer further includes a carrier gas flow regulator for separately controlling a flow rate of carrier gas to the vaporizer.

In one aspect of the invention there is provided a method for supplying vaporized sterilant to an enclosure. The method includes, at a first site, vaporizing a liquid sterilant to form sterilant vapor at a first rate of vaporization; at a second site, vaporizing a liquid sterilant to form sterilant vapor at a second rate of vaporization; providing streams of carrier gas to the first and second sites; injecting vaporized sterilant into a carrier gas at each site at independently adjustable rates; transporting the sterilant vapor from each site to different regions of the enclosure to be sterilized; and controlling vaporization through a plurality of interconnected control units, each control unit controlling an associated vaporizer to adjust independently the rate at which the associated vaporizer injects vaporized sterilant at each site so as to provide each of the regions with a selected concentration of sterilant vapor, wherein each control unit is controlled by a master control unit over a network of the interconnected control units to coordinate the aggregate injection of sterilant vapor.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

Figure 1:
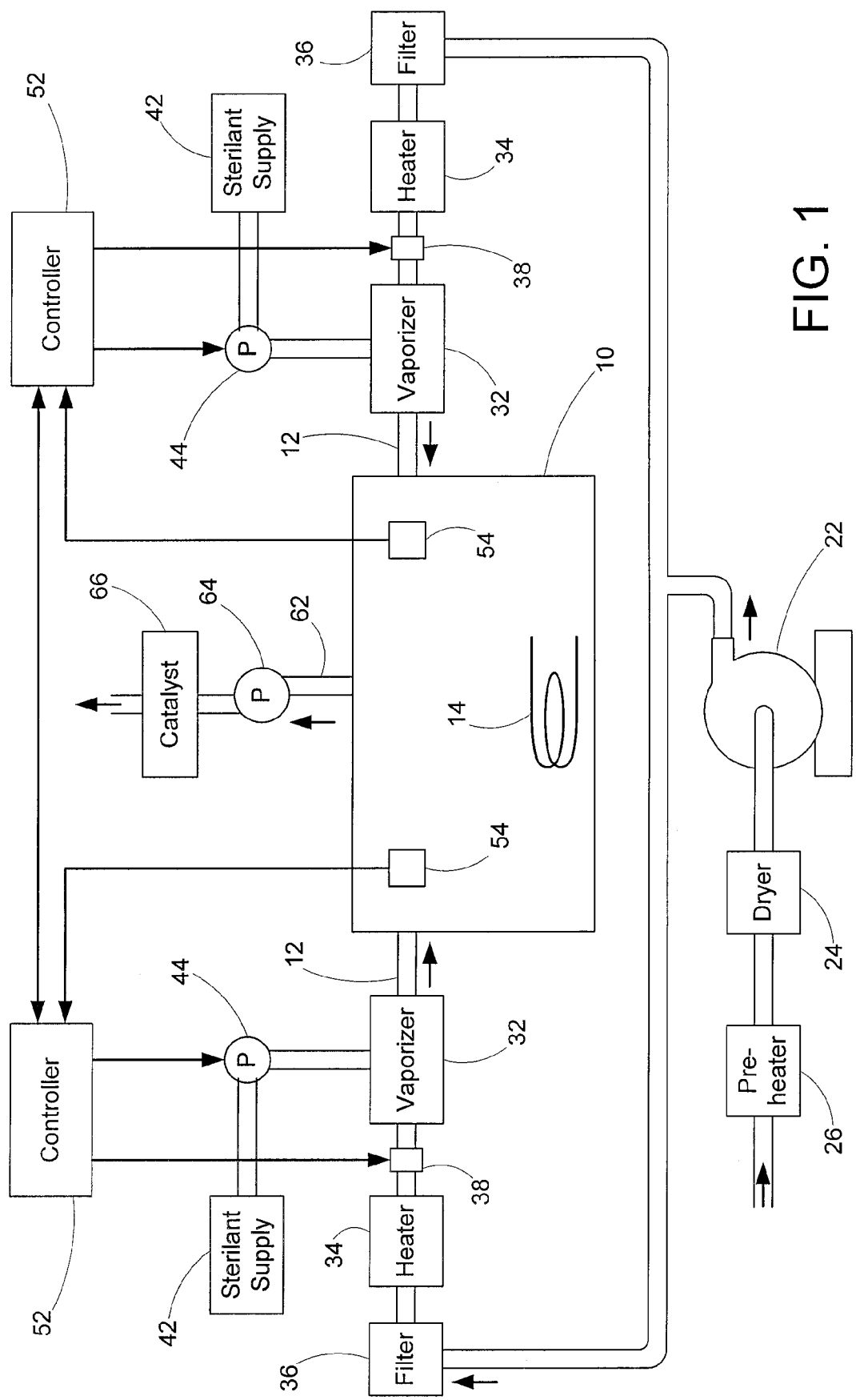
FIG. 1 is a schematic illustration of an embodiment of a vaporized hydrogen peroxide decontamination system according to the present invention.

The term "decontamination" shall be understood to include sterilization, disinfection and sanitization. For the purpose of describing the preferred embodiments herein the objective discussed will be sterilization, as that term is understood by those skilled in the art. Although the terms "decontamination" and "sterilization" may be used interchangeably herein, the system and method of the present invention are applicable to all levels of biological contamination control, whether referred to as sterilization, decontamination, disinfection, or otherwise. The terms "sterilant" and "decontaminant" are intended to include all liquid and gas sterilization, decontamination, disinfection, sanitization agents as understood by those skilled in the art.

All ranges and ratio limits disclosed in the specification and claims may be combined in any manner. It is to be understood that unless specifically stated otherwise, reference to an item in the singular may also include the item in the plural. All combinations specified in the claims may be combined in any manner.

Decontamination of a large and/or heterogeneous enclosure is best accomplished by using a plurality of decontaminant injection sites in a VHP system. As the size of the enclosure increases, the demand for hydrogen peroxide is increased and the efficiency of the vaporization system becomes more significant. The capacity of the vaporizer is limited in a number of ways. For instance, the vaporization process creates a pressure drop, reducing the flow of air through the vaporizer. This increases the sterilization time and effectively limits the size of the enclosure to one which is capable of sterilization within an acceptable time period. In addition, to maintain sterilization efficiency, the pressure at which the vapor is generated is limited to that at which the hydrogen peroxide is stable in the vapor state.

Further, large enclosures create problems themselves. Temperature differences throughout the chamber require different concentrations of the sterilant to compensate for condensation on cooler surfaces. Items within the enclosure require different concentrations of sterilant for optimum exposure because of their relative absorbencies. Pumping the vapor to more distant regions within the enclosure increases the extent of condensation within the vapor supply lines, reducing effectiveness.

Increasing the size of the vaporizer and the injection rate of hydrogen peroxide into the vaporizer may be helpful. However, the larger vaporizer still suffers from concentration variations and condensation concerns. Alternatively, decontamination of a large and/or heterogeneous enclosure may be accomplished by using a plurality of decontaminant injection points, either by injecting decontaminant at multiple locations from outside the enclosure or by placing multiple VHP generation systems throughout the enclosure. The rate of introduction of the decontaminant by the individual vaporizers may be adjustable within the enclosure.

Gaseous and vapor sterilization/decontamination systems rely on maintaining certain process parameters in order to achieve a target sterility or decontamination assurance level. For hydrogen peroxide vapor sterilization/decontamination systems, those parameters include the concentration of the hydrogen peroxide, the degree of saturation, the temperature and pressure and the exposure time. By controlling these parameters, the desired sterility assurance levels can be successfully obtained while avoiding condensation of the hydrogen peroxide due to vapor saturation.

The sterilization system of the present invention includes a plurality of decontaminant sources. The decontamination source may be, for example, a vaporizer for hydrogen peroxide (VHP). Each vaporizer is controlled locally, and the controllers for the vaporizers are interconnected via a communications network. Each vaporizer is provided with local sensors to provide feedback regarding the decontaminant concentrations and other process conditions to permit adjustment of the decontamination injection system for maintenance of the process conditions within the desired limits. In addition, the process conditions and/or settings may be adjusted to allow integration of the decontaminant concentrations so that the decontamination process can be continued until an appropriate dose of decontaminant has been delivered throughout the space being decontaminated.

With reference to FIG. 1, a plurality of vaporizers 32 inject vaporized hydrogen peroxide into a carrier gas. For the sake of simplicity, two vaporizers are illustrated, each with an associated localized controller. The number of vaporizers used in a particular decontamination system depends in part on the size and configuration of the enclosure. Hydrogen peroxide is pumped, preferably by an adjustable metering pump 44 from a cartridge or reservoir 42 and injected at a measured rate in droplets or mist form onto the heated plate of vaporizer 32. The hydrogen peroxide vaporizes on contact with the plate and is entrained in a flow of the carrier gas. The temperature of the plate is maintained at a temperature below that at which dissociation of the hydrogen peroxide occurs. A carrier gas flow regulator or baffle 38 adjustably controls the flow of carrier gas. Adjusting the metering pump 44 and the carrier gas flow regulator 38 controls the rate at which the hydrogen peroxide vapor is produced.

The carrier gas is preferably air, although other gases that are unreactive toward hydrogen peroxide are also contemplated. A carrier gas generator 22, such as a pump or container of pressurized gas, supplies the carrier gas to the vaporizers 32. When atmosphere air is the carrier gas, filters 36 remove contaminants. Preferably, a heater 34 raises the temperature of the carrier gas before it reaches the vaporizers 32, reducing condensation in the supply lines and raising the saturation concentration of hydrogen peroxide vapor. Optionally, a dryer 24 or the like controls the humidity of the carrier gas and preheater 26 preheats the carrier gas.

Supply lines 12 transport the mixture of carrier gas and vaporized hydrogen peroxide from the vaporizers 32 to an enclosure 10. To reduce the risk of condensation, the length of the supply lines 12 is minimized. To reduce the risk of condensation further, insulation and/or heaters may surround the supply lines 12. Optionally, two or more supply lines connect each vaporizer to two or more regions of the enclosure 10.

A vent 62 permits controlled release of excess pressure in the enclosure. Optionally, vacuum pump 64 evacuates the enclosure prior to hydrogen peroxide vapor introduction. Evacuation increases the rate at which hydrogen peroxide vapor can be drawn into the chamber, reducing the supply pressure of the hydrogen peroxide vapor and thereby avoiding condensation. A catalyst 66 or the like breaks down any residual hydrogen peroxide in the vented gas. Optionally, a heater 14 raises the temperature of and within the enclosure 10 prior to, and during, sterilization. Raising the temperature in the enclosure or at least its surfaces also reduces vapor condensation.

Sterilizable enclosures include microorganism-free work areas, freeze dryers, and pharmaceutical or food processing equipment. Whether high sterilization temperatures and or evacuation of the enclosure during sterilization are feasible depends on the construction of the enclosure and the nature of its contents. For example, sterilizable work areas are typically constructed of non-rigid plastic materials which do not withstand high temperatures and low pressures. Food processing equipment, in contrast, is often required to withstand high temperatures and pressures during processing operations and is more easily adapted to achieving more optimal sterilization conditions through evacuation and heating.

The hydrogen peroxide vapor is held in the enclosure 10 until sterilization is complete. Optionally, vacuum pump 64 draws out the hydrogen peroxide vapor from the enclosure following sterilization. This reduces the time required for dissipation of the hydrogen peroxide, and returns the enclosure to useful activity more quickly.

In the illustrated embodiment, the vaporizers are located at a distance from the carrier gas generator, in close proximity to the enclosure. The rate of introduction of hydrogen peroxide by the individual vaporizers is adjustable so as to optimize hydrogen peroxide vapor distribution within the enclosure.

Differences in temperature and absorbency of materials within the enclosure, flow patterns in the enclosure, and enclosure shape are among the factors influencing the optimum rate of introduction. The control system 50 regulates the introduction of hydrogen peroxide in accordance with local conditions within the enclosure as well as in accordance with predetermined integrated process settings. A plurality of monitors 54 monitor conditions within the enclosure 10. The monitors include temperature sensor 58, humidity sensor 72, vapor concentration sensor 56, air flow or turbulence sensor, pressure sensor, and the like.

Various sensing technologies may be used to monitor the process conditions within the enclosure. At least one sensor is used to determine the concentration of sterilant chemicals within the decontamination system. In one embodiment, the sterilization system uses an infrared (IR) sensor probe integrated into the control system which is thereby enabled to monitor the concentration of the hydrogen peroxide vapor at selected locations in or portions of the enclosure. The sensor probe provides for passage of a beam of electromagnetic radiation in the infrared region through the decontamination vapor in the sterilization enclosure. Some of the radiation is absorbed by the vapor, and the unabsorbed radiation is detected by a radiation detector sensitive to wavelengths of radiation in the IR region of the electromagnetic spectrum. The radiation detector determines the amount of radiation absorbed by the vapor, and provides an absorbance signal to a microprocessor which calculates the concentration of hydrogen peroxide vapor in the enclosure. An example of a monitor and control system that uses an IR sensor is described in U.S. Pat. No. 5,872,359, which is incorporated by reference herein.

In one embodiment, near infrared (NIR) spectroscopy is used to measure hydrogen peroxide concentration in the sterilization/decontamination system. Examples of this method of measuring vaporized hydrogen peroxide are described in U.S. Pat. Nos. 5,600,142; 5,847,392 and 5,847,393, which are incorporated by reference herein.

In another embodiment, the concentration of the liquid or gas decontaminant is measured during the sterilization cycle by a semiconductor-based sensor in fluid communication with the decontaminant. The sensor module includes a sensing element and integrated electronics that react to changes in the concentration of certain chemicals to which the element is exposed. The electronics and the software associated with the module can be configured to react to a target chemical compound. Any semiconductor-based sensor module, and its associated software, that is selective for and sensitive to the particular liquid or gas used as the decontaminant may be adapted for use in the invention.

The semiconductor-based sensor may be used in connection with any suitable liquid or gas sterilant that is detectable by a semiconductor sensing system including, but not limited to ethylene oxide gas, liquid and gaseous hydrogen peroxide, liquid and gaseous formaldehyde, liquid and gaseous peroxygen compounds, ozone, alcohol, glutaraldehyde, ammonia and mixtures of these.

An exemplary sensor is described in U.S. Pat. No. 6,844,742, which is incorporated by reference herein. This sensor includes a capacitor that acts as a sensing element. Electrical properties of the capacitor are responsive to a sterilant chemical used in the system. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

Another exemplary sensor is described in U.S. Pat. No. 7,232,545, which is incorporated by reference herein. This sensor includes an element having a layer or coating of a material that interacts with, or is reactive with, a sterilant chemical used in the decontamination system, such that mechanical motion or movement of the element is converted into an electrical signal. The element may be a moving or suspended component, but in a preferred embodiment, the element is a piezoelectric device, and more preferably, is a quartz crystal. Other piezoelectric materials, such as by way of example and not limitation, include Rochelle salt, barium titanate, tourmaline, polyvinylidene fluoride and crystals that lack a center of symmetry.

A control system regulates the introduction of sterilant to the enclosure. Each local decontamination system includes a sterilant supply, a vaporizer, a flow regulator, a monitor and a control unit. The control unit is a system microprocessor or microcontroller programmed to control the operation of the local decontamination system. The control unit may be in accordance with any conventional controller. The control unit preferably includes (or is connected with) a data storage device for storing data.

Figure 2:
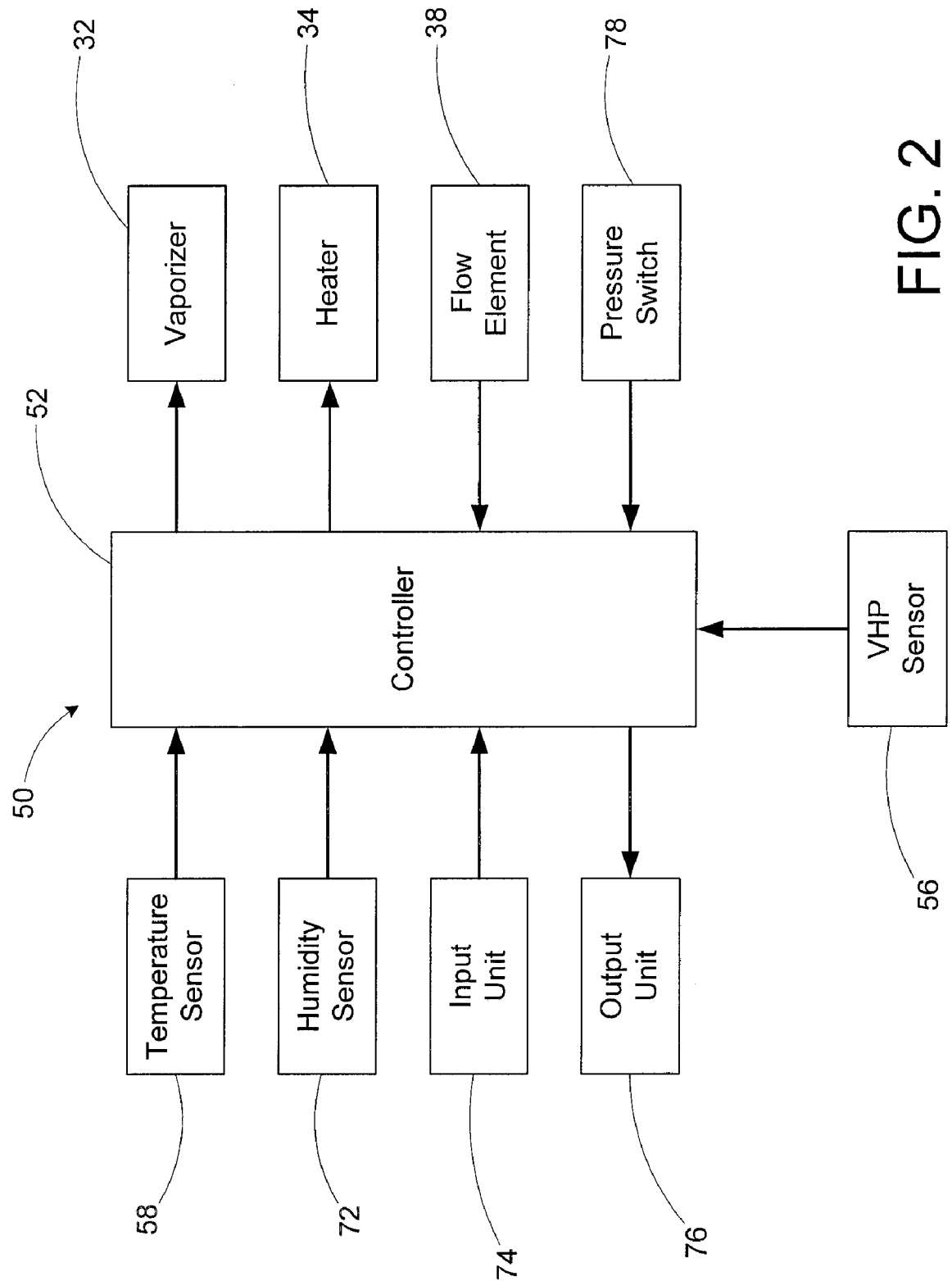
FIG. 2 is a schematic illustration of a control system for a localized decontamination system shown in FIG. 1.

Referring to FIG. 2, a control system 50 for controlling the operation of the localized decontamination system is schematically illustrated. Control system 50 includes controller 52 that controls the operation of the motor that drives pump 44. Controller 52 also monitors VHP sensor 56, pressure switch 78, VHP temperature sensor 58, flow element 38 and humidity sensor 72. Controller 52 also controls the operation of heater 34 and vaporizer 32.

An input unit 74 may be provided to allow a user of the localized decontamination system 30 to input operation parameters. The input unit 74 is typically connected to the controller that functions as the master controller among the plurality of controllers. Input unit 74 may be any device that would facilitate the input of data and information to controller 52 by a user of system 30, such as by way of example and not limitation, a keypad, a keyboard, a touch screen, switches, or signals. An output unit 76 may be provided to enable controller 52 to provide information to the user on the operation of system 30. Output unit 76 may be, by way of example and not limitation, a printer, a display screen or LED display or signal. Controller 52 is programmed such that system 30 operates in certain operating phases while maintaining certain preferable operating conditions.

Typical sterilization/decontamination cycle includes a drying phase, a conditioning phase, a decontamination phase and an aeration phase. Prior to the initiation of a sterilization/decontamination cycle, input unit 74 is used to provide the operational parameters to controller 52. The operational parameters include a target humidity level for a drying phase, a target VHP concentration for a conditioning phase, a target humidity level and a target VHP concentration for a decontamination phase, and a target VHP concentration for an aeration phase.

Each decontamination system 30 is capable of operating under its own control system 50 when operating singly. By connecting the control units 52 together via communication cables or the like, the systems create an integrated network and act in concert.

Having each of the localized decontamination systems 30 react to the prevailing local decontamination conditions ensures complete decontamination throughout the space or enclosure being treated, while ensuring that excessive doses of decontaminant are not delivered in areas where there is little challenge to the delivery of the decontaminant.

Figure 3:
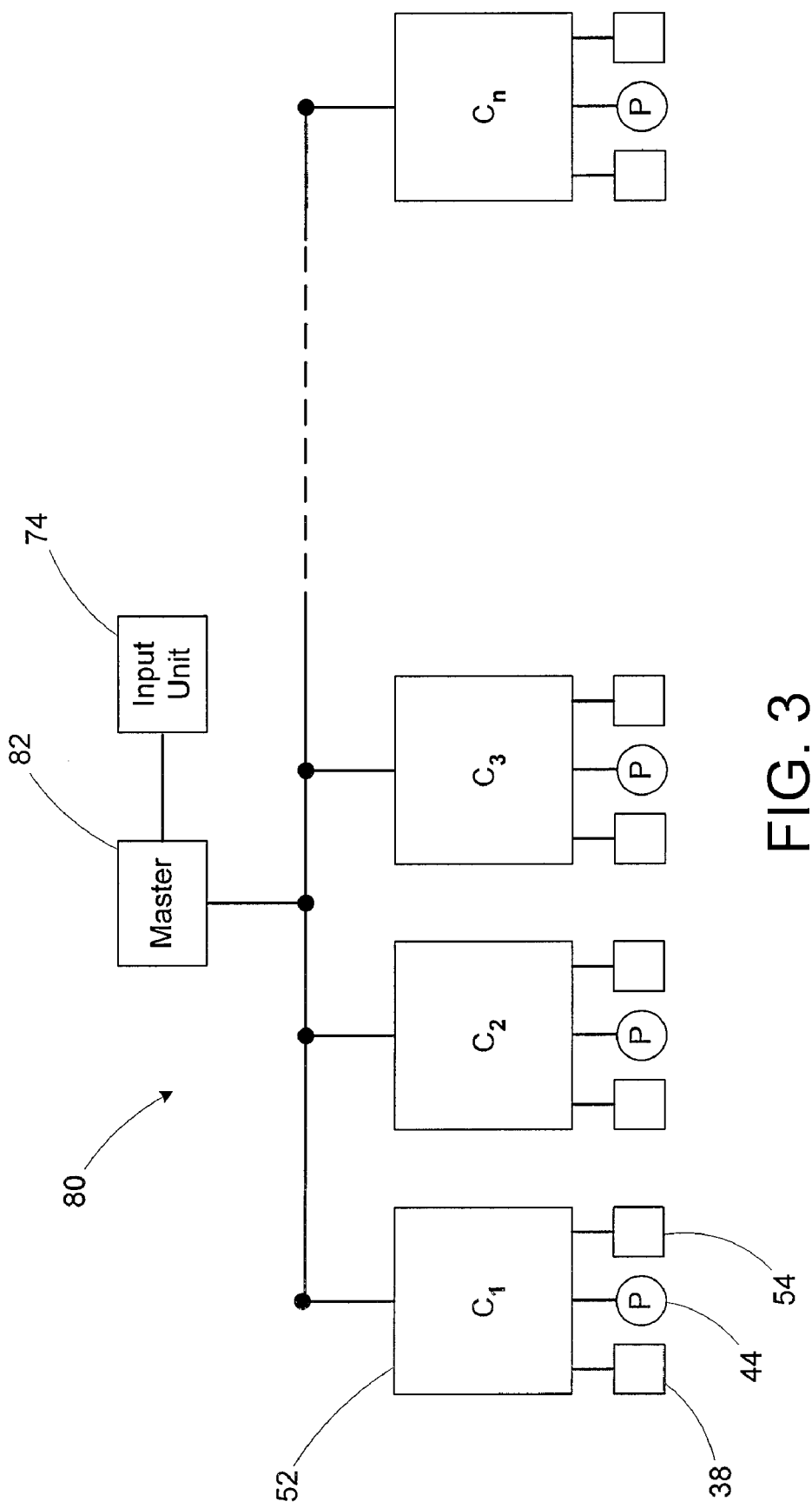
FIG. 3 is a schematic illustration of a control system network for a decontamination system.

Referring to FIG. 3, each of the localized control units 52 are connected via a network 80. In this embodiment, the network includes a master controller 82 connected to each of n control units $C_1$ to $C_n$, that communicate with each other through the master unit 82. This network arrangement may be referred to as a "master-slave" arrangement wherein the master controller 82 is the master and the control units $C_1$ to $C_n$ represent the slaves.

Figure 4:
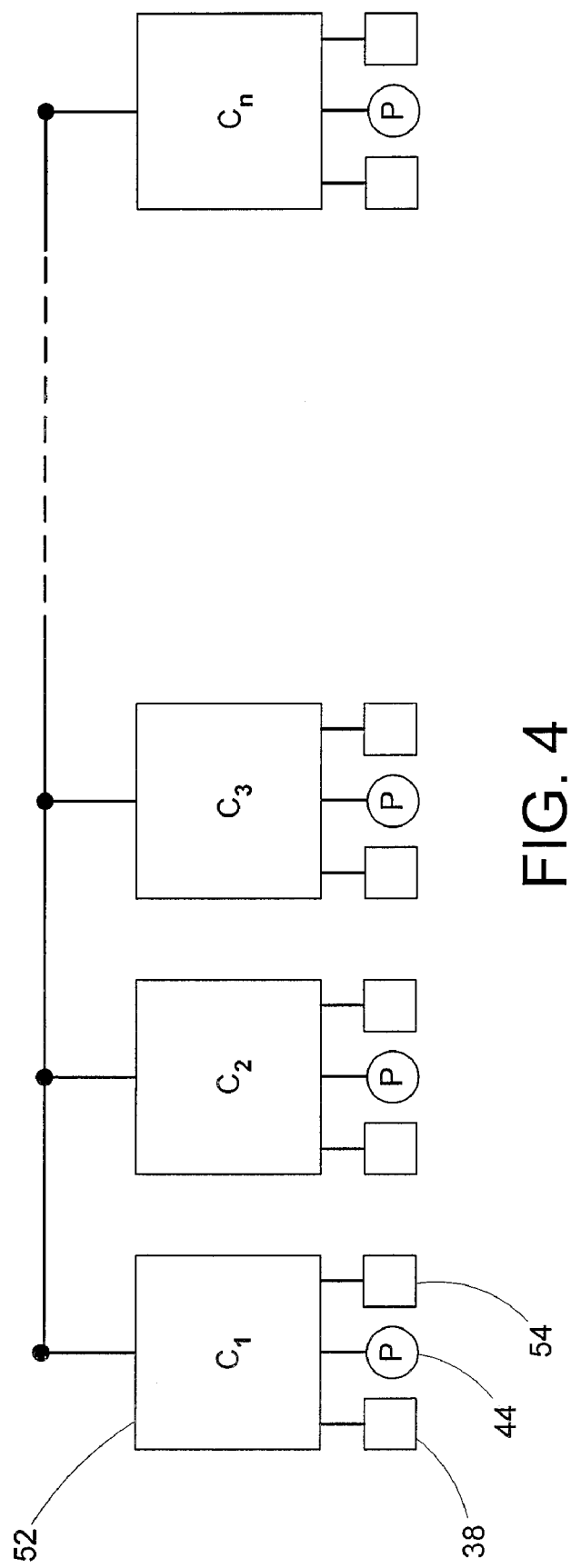
FIG. 4 is a schematic illustration of another modified embodiment of a control system network for a decontamination system.

Referring to FIG. 4, in another embodiment, the localized control units 52 are connected to each other serially, such that the control interface at one of the termini of the series automatically becomes the master controller for all of the units 52 connected via the network, and all of the remaining control units accept control from the master controller. This network arrangement may be referred to as a "peer" arrangement. For example, control unit $C_1$ may act as the master controller. If control unit $C_1$ should fail, lose power, experience difficulty in computing signals or otherwise become inoperable, control unit $C_2$ may serve as backup, becoming the master controller. Any one of the other control units may serve as the master controller. To assist in determining which control unit 52 is best suited to be the master controller, the control units may share health and status information with one another, including self-diagnostic data and cross-diagnostic data. In one embodiment, a determination to switch master and backup controller responsibilities is made by the control unit that is currently the master controller. Having the networked controllers automatically determine which control unit is the master and automatically accept process conditions from that control unit greatly simplifies the set up and operation of the distributed decontamination system. Allowing any number of control units to be interconnected simplifies set up for the user.

It should be appreciated that while a preferred embodiment of the present invention has been described with reference to a sterilant comprised of hydrogen peroxide and water, it is contemplated that sterilant comprised of other chemical components may also be used in connection with the present invention. These other chemical components may include deactivating chemicals, including, but not limited to, chemicals selected from the group consisting of: hypochlorites, iodophors, quaternary ammonium chlorides (Quats), acid sanitizers, aldehydes (formaldehyde and glutaraldehyde), alcohols, phenolics, peracetic acid (PAA), and chlorine dioxide.

Specific examples of sterilant chemicals, include, but are not limited to, liquid hydrogen peroxide, peracids such as peracetic acid, bleach, ammonia, ethylene oxide, fluorine containing chemicals, chlorine containing chemicals, bromine containing chemicals, vaporized hydrogen peroxide, vaporized bleach, vaporized peracid, vaporized peracetic acid, ozone, ethylene oxide, chlorine dioxide, halogen containing compounds, other highly oxidative chemicals (i.e., oxidants), and mixtures thereof.

The sterilant chemicals may also be combined with other chemicals, including, but not limited to, water, de-ionized water, distilled water, an alcohol (e.g., a tertiary alcohol), a glycol-containing chemical compound, and mixtures thereof. Glycol-containing chemical compounds include, but are not limited to, polyethylene glycol, diethylene glycol, triethylene glycol, tetraethylene glycol, glycol ethers, polypropylene glycol, propylene glycol, de-ionized water vapor, distilled water vapor, a vaporized alcohol (e.g., a tertiary alcohol), and mixtures thereof. These chemicals may act as carrier fluids or diluents.

Vaporous hydrogen peroxide (VHP), which may be generated from an aqueous solution of hydrogen peroxide, may be used as the decontaminant. By adding an alkaline gas that is soluble in the hydrogen peroxide (ammonia, for example), the pH of the decontaminant may be controlled. VHP, when used in combination with ammonia gas, may be referred to as modified VHP or mVHP. VHP and/or mVHP may be effective microbial and chemical decontaminants because they may provide a broad spectrum of activity against a wide variety of pathogenic microorganisms and chemical pathogenic agents, such as hard to destroy spores of *Bacillus stearothermophilus*, *Bacillus anthracis*, smallpox virus, and the like. They may be also effective at or close to room temperature (e.g., about 15 to about 30° C.), making them suitable for use in the decontamination enclosure 10 with little or no heating. VHP and/or mVHP may have good material compatibility, rendering them safe for use with a variety of equipment and materials, including electronic equipment, soft furnishings, brass and chrome fixtures, and the like. VHP may degrade to water and oxygen over time, which may not be harmful to a person subsequently entering the decontamination enclosure 10. Low levels of hydrogen peroxide (for example, about 1 ppm, or less) that may remain in the decontamination enclosure 10 after the decontamination process has been completed may not be considered to pose a risk to a person entering the enclosure.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

The invention claimed is:

1. A sterilization system, comprising:
   a source of a liquid sterilant;
   a plurality of vaporizers that independently inject vaporized sterilant into a carrier gas at differently adjustable rates, each vaporizer including a separate liquid sterilant regulator for simultaneously, variably, and independently controlling a rate of injection of sterilant into the vaporizer;
   at least one supply line for transporting the sterilant vapor from each vaporizer to different regions of an enclosure to be sterilized; and
   a network of interconnected controllers comprising (a) a plurality of serially interconnected control units, each control unit controlling an associated vaporizer to adjust independently the rate at which the associated vaporizer injects vaporized sterilant so as to provide each of the regions with a selected concentration of sterilant vapor, and (b) a master control unit configured to control each control unit over the network to coordinate the aggregate injection of sterilant vapor;
   wherein the master control unit is one of the plurality of control units and any one of the plurality of control units can become the master control unit for all of the control units; and
   wherein the network of interconnected controllers automatically determines which control unit is the master control unit and all of the remaining control units automatically accept process control from the master control unit.

2. The sterilization system of claim 1 further comprising a plurality of monitors for detecting conditions in each of the different regions of the enclosure, wherein the network of interconnected controllers controls the rate at which each vaporizer injects vaporized sterilant into the carrier gas in accordance with the detected conditions in the different regions.

3. The sterilization system of claim 2, wherein the detected conditions are chosen from temperature, pressure, relative humidity, air flow velocity, sterilant concentration and combinations thereof.

4. The sterilization system of claim 1 wherein the sterilant comprises hydrogen peroxide.

5. The sterilization system of claim 4 wherein the sterilant comprises vaporous hydrogen peroxide and ammonia.

6. The sterilization system of claim 1 wherein each vaporizer further includes a carrier gas flow regulator for separately controlling a flow rate of carrier gas to the vaporizer.

7. A method for supplying vaporized sterilant to an enclosure, comprising:
- at a first site, vaporizing a liquid sterilant to form sterilant vapor at a first rate of vaporization;
- at a second site, vaporizing a liquid sterilant to form sterilant vapor at a second rate of vaporization;
- providing streams of carrier gas to the first and second sites;
- injecting vaporized sterilant into a carrier gas at each site at independently adjustable rates;
- transporting the sterilant vapor from each site to different regions of the enclosure to be sterilized; and
- controlling vaporization through a plurality of interconnected control units, each control unit controlling an associated vaporizer to adjust independently the rate at which the associated vaporizer injects vaporized sterilant at each site so as to provide each of the regions with a selected concentration of sterilant vapor, wherein each control unit is controlled by a master control unit over a network of the interconnected control units to coordinate the aggregate injection of sterilant vapor;
- wherein the master control unit is one of the plurality of control units and any one of the plurality of control units can become the master control unit for all of the control units; and
- wherein the network of interconnected controllers automatically determines which control unit is the master control unit and all of the remaining control units automatically accept process control from the master control unit.

8. The method of claim 7 wherein the sterilant comprises hydrogen peroxide.

9. The method of claim 8 wherein the sterilant comprises vaporous hydrogen peroxide and ammonia.

* * * * *